United States Patent
Ray et al.

[11] Patent Number: 6,036,659
[45] Date of Patent: Mar. 14, 2000

[54] COLLECTION DEVICE FOR BIOLOGICAL SAMPLES AND METHODS OF USE

[75] Inventors: Robert A. Ray, Stuart; Robert Stangarone, Boca Raton; Julie Peddicord, Jensen Beach; Raul Sarzo, Port St. Lucie, all of Fla.

[73] Assignee: FlexSite Diagnostics, Inc., Palm City, Fla.

[21] Appl. No.: 09/169,843

[22] Filed: Oct. 9, 1998

[51] Int. Cl.⁷ ........................................................ A61B 5/00
[52] U.S. Cl. ............................................................ 600/573
[58] Field of Search .................................... 600/573, 575, 600/584; 604/403, 406; 422/50, 56, 58; 436/74, 169, 170

[56] References Cited

U.S. PATENT DOCUMENTS

| | | |
|---|---|---|
| 4,260,392 | 4/1981 | Lee . |
| 4,277,249 | 7/1981 | Broughton . |
| 4,299,812 | 11/1981 | Coombes . |
| 4,654,127 | 3/1987 | Baker et al. . |
| 4,678,757 | 7/1987 | Rapkin et al. . |
| 4,685,472 | 8/1987 | Muto ...................................... 600/573 |
| 4,738,823 | 4/1988 | Engelmann . |
| 4,753,776 | 6/1988 | Hillman et al. . |
| 4,774,192 | 9/1988 | Terminiello et al. . |
| 4,790,979 | 12/1988 | Terminiello et al. . |
| 4,810,394 | 3/1989 | Masuda . |
| 4,816,224 | 3/1989 | Vogel et al. . |
| 4,845,132 | 7/1989 | Masuoka et al. . |
| 4,933,092 | 6/1990 | Aunet et al. . |
| 4,987,085 | 1/1991 | Allen et al. . |
| 5,004,584 | 4/1991 | Rayman . |
| 5,084,173 | 1/1992 | Nitadori et al. . |
| 5,130,258 | 7/1992 | Makino et al. . |
| 5,135,719 | 8/1992 | Hillman et al. . |
| 5,139,685 | 8/1992 | de Castro et al. . |
| 5,204,267 | 4/1993 | Sangha et al. . |
| 5,260,221 | 11/1993 | Ramel et al. . |
| 5,262,067 | 11/1993 | Wilk et al. . |
| 5,264,180 | 11/1993 | Allen et al. . |
| 5,266,219 | 11/1993 | Pall et al. . |

(List continued on next page.)

OTHER PUBLICATIONS

Guthrie, R., et al., A Simple Phenylalanine Method for Detecting Phenylketonuria in Large Populations of Newborn Infants, Pediatrics 32(3): 338–343 (1963).
Eross, J., et al., Colorimetric measurement of glycosylated protein in whole blood, red blood cells, plasma and dried blood, Ann. Clin. Biolchem, 21: 477–483 (1984).
Little, et al., Collection of Blood on Filter Paper for Measurement of Glycated Hemoglobin by Affinity Chromatography, Clin. Chem. 42(5): 869–871 (1986).
Voss, et al., Stability and Accuracy Evaluation of a Capillary Collection System for Hemoglobin A1c Specimens, Clin. Chem. 37(6): 988, Abstract 0373 (1991).
Voss, et al., Evaluation of Capillary Collection System for HbA1c Specimens, Diabetes Care 15(5): 700–701 (1992).
Jeppsson, et al., Capillary Blood on Filter Paper for Determination of HbA1c by Ion Exchange Chromatography, Diabetes Care 19(2): pp. 142–145 (1995).
Niederau, et al., Evaluation of a Non–Liquid Transportable Device for Capillary Blood Suitable for HbA1c Determination, Clin. Cheml 42(6): 167, Abstract 0297 (1996).

(List continued on next page.)

*Primary Examiner*—Max Hindenburg
*Attorney, Agent, or Firm*—Quarles & Brady LLP

[57] ABSTRACT

A device for remote-site biological sample collection for laboratory analysis is described. The device can be made in several configurations which all include separate members for collecting and separating the biological sample into its desired components which are detected or measured. Methods of use for the device are also described.

25 Claims, 15 Drawing Sheets

U.S. PATENT DOCUMENTS

| | | |
|---|---|---|
| 5,340,539 | 8/1994 | Allen et al. . |
| 5,415,758 | 5/1995 | Comeau . |
| 5,416,000 | 5/1995 | Allen et al. . |
| 5,427,953 | 6/1995 | Yee . |
| 5,432,097 | 7/1995 | Yourno . |
| 5,443,080 | 8/1995 | D'Angelo et al. ............. 600/573 |
| 5,460,057 | 10/1995 | Østrup . |
| 5,460,777 | 10/1995 | Kitajima et al. . |
| 5,496,626 | 3/1996 | Hamajima et al. . |
| 5,508,200 | 4/1996 | Tiffany et al. . |
| 5,516,487 | 5/1996 | Rosenthal et al. . |
| 5,665,238 | 9/1997 | Whitson et al. . |
| 5,676,144 | 10/1997 | Schoendorfer ............. 600/573 |
| 5,725,774 | 3/1998 | Neyer . |

OTHER PUBLICATIONS

Little, et al., Filter Paper Collection of Blood for Measurement of HbA1c Immunoassay, Clin. Chem. 42(6): 193, Abstract 0404 (1996).

Marsden, et al., The Comparative Performances of Whatman BFC 180 and S&S 903 Filter Papers in Newborn Screening Assays for Immunoreactive Trypson, 17–OHP and Galatcose, Third Meeting of the International Society for Neonatal Screening and 12th National Neonatal Screening Symposium, Boston, Massachusetts (Oct. 21–24, 1996).

Vohra, et al., Efficacy of New Filter Paper in a State Newborn Screening Program, Third Meeting of the International Society for Neonatal Screening and the 12th National Neonatal Screening Symposium, Boston, Massachusetts (Oct. 21–24, 1996).

Duddy, et al., The Evaluation of Whatman BFC180 Blood Collection Paper Against Two Alternative Products, Third Meeting of the International Society for Neonatal Screening and the 12th National Neonatal Screening Symposium, Boston, Massachusetts (Oct. 21–24, 1996).

COLLECTION DEVICE FOR BIOLOGICAL SAMPLES AND METHODS OF USE

BACKGROUND OF THE INVENTION

The subject invention relates to a device and method for collection, transport, storage, processing (e.g., separation of cells from serum), and compatibility with laboratory analysis of a biological sample obtained from a living organism. In particular, the subject invention relates to a device and method used in the analysis of a biological component in a dried blood or urine sample obtained from an animal.

In laboratory and clinical settings, it is often necessary to take, contain, transport, and store biological samples, such as blood or blood products, for purposes of analysis of various components in the sample. The analysis of biological fluids to confirm the levels or concentrations of various components contained therewithin is an accepted clinical practice for the determination of proper functioning of various biological systems. Liquid sample collection, handling, transport, and storage, which is the conventional approach, has many problems associated with it including: (1) the risk of container breakage or leakage which causes loss of sample and the danger of infection; (2) sample instability during shipment and storage; (3) refusal of transport carriers to accept liquid biohazardous shipments; and (4) collection of more sample than is necessary for testing, to ensure quantities compatible with common laboratory methods of serum or plasma preparation and subsequent analysis.

To overcome these problems, in one approach, a biological sample, e.g., a drop or two of whole blood, has been collected on filter paper and dried prior to transport. These dried blood spot samples are mailable and are accepted by all common carriers. Despite the improved handling of dry samples, however, analysis of certain dissolved blood components is not currently possible from a whole blood sample unless the red blood cells are first separated from the blood plasma or serum. The most conventional manner of separating serum or plasma from blood cells is by centrifugation.

In the case of certain blood component determinations, the handling of the blood samples can also be a critical part of the ultimate accuracy of measurement in the sample. Therefore, even when a blood sample is removed from the body, the concentration of the component within a liquid blood sample can change over time. Dried blood spots have the advantage of helping to preserve certain components for later analysis.

There is currently a need for a simple, yet accurate device for collection, transport, preparation, and storage of a dried blood plasma or serum sample from whole blood, for subsequent extraction and analysis of components in the dried plasma or serum sample. Testing in the laboratory affords more sophisticated equipment, highly trained personnel, professional quality control, and cost effective solutions.

BRIEF SUMMARY OF THE INVENTION

The subject invention concerns a device for use in collection, separation, stabilization, preservation, transport, storage, and elution of a biological sample for laboratory analysis of particular components in the sample, methods of use for the device, and kits comprising the device.

Specifically, the subject invention concerns a device which is useful for collection of a whole blood sample, allowing separation of the blood cells from the blood serum or plasma, drying the blood serum or plasma sample on the device, transporting the collected and dried blood serum or plasma sample to a laboratory or other facility for analysis, and extracting an analyte of interest from the sample for determining presence or absence of the analyte or, if present, the concentration thereof.

Briefly, one embodiment of the subject device comprises a plurality of separate components, including a quantitation member for facilitating delivery of a particular volume or amount of sample to a collection member. The sample can also be passed through another component, e.g., a separation member which can separate certain undesirable components from the components of interest in the sample. For example, blood cells, e.g., red blood cells, can be separated from blood plasma or serum containing an analyte which is to be tested for, or measured. The collection member, which can be an absorbent or non-absorbent filter or membrane material, can serve to collect the component of interest in the sample, e.g., serum or plasma, provide a surface for drying of the component of interest, and a means for storage of that component for subsequent transport to, and analysis in, a laboratory. The device can have a plurality of any one of the quantitation, separation, or collection members.

One preferred embodiment has a plurality of separation members, including one which also can be useful as a quantitation member. Specifically, the quantitation member serves to collect overflow of sample so that a defined volume of sample component of interest is delivered to the collection member, over which the other described members are superimposed. For example, the separation/overflow member can be a track etched membrane, as is well-known in the art, or can be a screen material which can spread the liquid sample such that a particular volume of the sample is provided in each cell of the screen. This embodiment is termed the "multilaminate configuration."

In one such embodiment of the multilaminate configuration, namely, the "trilaminate configuration," a separation member is contactingly disposed above or below a layer of material which provides a spreading or quantitative effect for the separated serum or plasma. The separated serum or plasma then absorbs into or adsorbs onto a collection member disposed below the spreading or quantitative material and the separation member. Thus, the trilaminate configuration comprises a substantially three-layered collection device, having a separation member, a quantitation member, and a collection member.

Alternatively, in certain embodiments of the subject invention, the quantitation member can be a material having a wicking property, e.g., standard capillary tube such as is used in routine laboratory work (typical volumes are 5–50 microliters), or can be an absorbent or non-absorbent material which has quantitative liquid volume properties for liquids, or an encased fiber bundle or other like configuration which accepts a quantitative liquid uptake and can deliver a predetermined volume of sample to another component of the device.

The separation member can be an absorbent, adsorbent, non-absorbent, or non-adsorbent material, for delivering the sample to the serum/plasma collection member via capillary action. The separation member can also provide a separation function for selectively separating different components within the sample, or can provide a quantitative volumetric measurement function. The separation member, useful for separating a component of interest from an undesired component in the biological sample prior to introduction of the component of interest to the collection member, according to one embodiment, can be a substantially circular section of absorbent filter paper having a predetermined standard size.

In one embodiment, a device according to the subject invention comprises a first wicking or quantitation member and a second "separation member," as described. A third "collection member" component is substantially circular and disposed in contact with the separation member for collecting sample therefrom. Preferably, a device of this embodiment is configured to include a substantially circular collection member contacting a substantially circular separation member which is contactingly disposed between the quantitation or wicking member and the circular collection member. This configuration is referred to herein as a "dual pad" configuration.

The members, namely, the quantitation member, the separation member, and the collection member, must contact one another for transferring the sample from one member to the other. These members can be abutted to one another, can overlap, or can be superimposed over one another. The separation member and collection member are typically substantially similar in diameter; the separation member which also serves as an overflow quantitation member can be substantially the same size or larger in diameter than the collection member. The separation and collection members can have thicknesses, absorbencies, or migration or other physical properties different from one another in order to produce a particular desired effect or result.

In an alternative embodiment, the quantitation member is typically a capillary tube, the separation member is typically a substantially circular section of absorbent filter or chromatography paper having cell separating properties and a predetermined, standard size; and the collection member is an elongate strip of absorbent material, e.g., filter chromatography paper. Thus, the subject device, having the circular separation member and elongate collection member in contact with one another, is configured having two "stems" or "handles" diametrically opposed to one another. This configuration is termed the "single pad" configuration. This embodiment is used by obtaining a small amount of a biological sample to be tested, e.g., a drop of blood from a sterile lancet fingerstick, and bringing the sample in contact with the wicking or quantitation member. The sample then wicks into the separation member and separates into particular components whereby the components of interest migrate to and are retained on the elongate collection member.

In another alternative configuration, termed the "lateral flow configuration," the quantitation or wicking member can be eliminated. The sample, e.g., whole blood, is applied directly to the separation member, and the collection member achieves quantitation by uniformly distributing the serum or plasma in the collection member so that a fixed area of collection member contains a quantitative amount of serum or plasma. A collector of absorbent material, e.g., HemaSep L (Gelman), or a non-adsorbent screen, such as Nitex 3-8/1 (Tetko), can function in such a manner.

For each of these configurations or embodiments, it is preferred to include a cover for at least the collection member and, more preferably, a cover which substantially envelopes the separation member and collection members, except for an aperture or perforation through which the separation member communicates with the outside environment. This aperture further provides a means for applying a liquid sample directly to the separation member if desired. In the case of the dual pad configuration, it is preferable to provide a cover over the separation and collection members, with a perforation or aperture provided over the separation member.

Preferably, the cover comprises a pair of plastic sheets which are superimposed over one another to form a laminated device. At least one of the sheets can have adhesive disposed on one of its facing surfaces so that the sheets can be adhered together around substantially the entire perimeter of the separation and/or collection members. The quantitation or wicking member can extend from the laminated sheets, forming an uncovered "tail". In a preferred embodiment, one of the sheets covering the dual pad configuration is perforated to allow air to reach the separation member to facilitate drying of the sample-saturated separation member prior to transport of the collected sample to a facility for analysis. This advantageously can prevent spillover or undesired migration of separated components, e.g., red blood cells, retained in the separation member to the collection member.

In certain embodiments, at least one additional layer of plastic sheet can be disposed between two members of the device. For example, in one embodiment of the multilaminate configuration, a layer of plastic sheet is disposed between opposing faces of a screen member and a separation member.

The plastic layer so disposed must provide a means for allowing fluid communication between the screen and separation member. Thus, an aperture or pore can be provided to allow sample to migrate from one member to another member, including the collection member.

A centered aperture or pore in this additional plastic layer, wherein the aperture or pore is substantially smaller than the surface area of the receiving face of a juxtaposed separation member, can facilitate directly the sample to that juxtaposed member and can control volume of sample ultimately received by the collection member.

The subject method begins with the application of a sample, e.g., a drop of whole blood (or "blood spot"), typically procured by a fingerstick using a lancet, to the device by bringing the sample into contact with a quantitation or a separation member, allowing certain components of the sample to selectively migrate to the collection member, and drying the collection member containing the collected sample or allowing it to dry by exposure to air over a period of time, e.g., overnight. The dried sample then can be mailed to the analytical laboratory for determination of presence, absence, or quantity of analyte present in the sample.

Upon receipt of the sample, the analytes contained by the collection member can be physically separated or extracted from the collection member and used for quantitative or qualitative analysis of one or more of those analytes. Advantageously, the subject device can perform at least two functions: (1) as a blood collection means and (2) as a blood transport medium for subsequent clinical analysis.

One objective of this invention is to eliminate problems encountered with currently used devices or methods, including providing a device and method wherein variation of sample size is minimized when absorbed onto a filter paper.

Another object of this invention is to provide for satisfactory drying of the sample prior to packaging and transport of the sample to a laboratory or other facility for analysis.

The subject invention further concerns a kit for enabling an individual to collect a sample and transport it to a facility for analysis. In general, the kit, comprising at least one of the above-described devices and instructions for use of the device, can further include components selected from the following: lancet, antiseptic swab, transport packaging, or an information card for providing information, e.g., medical history or health status, of the individual being tested.

DETAILED DESCRIPTION OF THE PREFERRED EMBODIMENTS

The subject invention concerns a device which can be useful for collection, separation, stabilization or preservation, transport, storage or elution, of components of interest in a biological sample for laboratory analysis of an analyte contained in that sample component. The subject device comprises a separation member for separating and retaining, without leaching from the separation member, an undesired component (e.g., cells), from a component of interest (e.g., serum or plasma) that constitute the sample. The particular component of the sample which is to be analyzed is termed an analyte, which is typically contained within, and is collected with, the component of interest, namely, serum or plasma in a sample of whole blood.

For purposes of this invention, the terms "serum" or "plasma" can be used interchangeably and would be understood by those of ordinary skill in the art to refer to a blood sample having certain cellular components removed or separated therefrom. The serum or plasma containing the analyte selectively migrates through the separation member and becomes retained or "collected" in a second component of the subject device, namely, an absorbent or non-absorbent collection member.

The collection member comprises a membrane on which the sample can be collected, stored, or transported, and further can be eluted or analyzed therefrom. Preferably, the collection member is a material which allows the analyte to be extracted or eluted from the membrane using standard chemistry procedures for subsequent quantitative or qualitative analysis.

Figure 1:
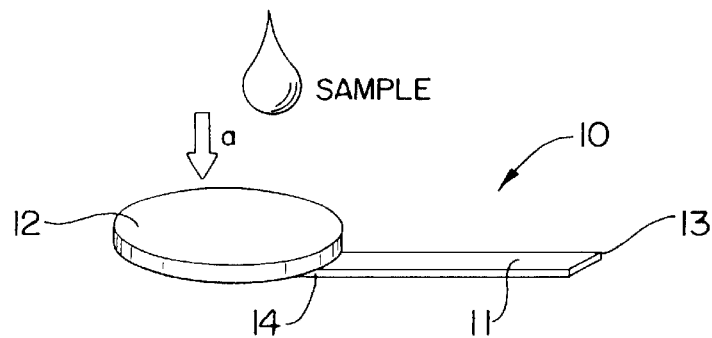
FIG. 1 shows a perspective view of one embodiment ("lateral flow" configuration) of a device according to the subject invention.

A first embodiment for the subject invention is shown in FIG. 1 wherein the device 10 comprises a collection member 11 having a first free end 13 and a second end 14 contacting a separation member 12. The collection member 11 and separation member 12 preferably contact one another in an overlapping manner so that a sample placed onto the separation member 12 can migrate, e.g., via capillary action, toward the collection member 11 so that analyte in the sample, selectively separated from an undesired component, is delivered to, and absorbed into, the collection member. Most preferably, the collection member is positioned to overlap with the separation member wherein the second end of the collection member contacting the separation member is disposed approximately in the center of the separation member. The opposite or free end of the collection member is allowed to extend away from the separation member to form a "tail".

In one embodiment, the separation member can be pre-saturated or pre-treated with a reagent which facilitates separation of an undesired component in the sample from the component of interest which can contain analyte. For example, in a device of the subject invention useful for collection, storage, transport, or analysis of a blood plasma or serum analyte, the separation member can be pre-treated with a reagent which retards migration of red blood cells or a reagent such as a surfactant which facilitates flow of sample through the separation member. For a serum analyte, for example, a reagent which agglutinates red blood cells can be used to pre-treat the separation member in the sample, so that a clotting cascade is initiated in a whole blood sample placed on the separation member, retarding movement of the red blood cells to the collection member so that blood serum containing an analyte of interest first reaches and substantially saturates the collection member. This advantageously eliminates the need to separate serum from a whole blood sample by more labor-intensive methods, e.g., by centrifugation.

In a most preferred embodiment for use with a whole blood sample, the separation member can be pre-treated with a red blood cell agglutinating reagent, e.g., a lectin such as concanavalin A or the like, typically less than 1% concentration, to facilitate separation of the red blood cells from the blood serum. As migration of red blood cells is slowed through the separation member 31, serum which can contain an analyte of interest can continue to migrate through the separation member 31 and onto collection member 34 whereby the collection member can become at least partially or, preferably, substantially saturated with serum for subsequent analysis.

It would be understood by those of ordinary skill in the art that other reagents which selectively bind or retard movement of certain other biological sample constituents can also be used for pre-treating the separation member. For example, the separation member can be pre-treated with a reagent which separates unclotted red blood cells from plasma so that plasma proteins, e.g., clotting factors, can be measured or analyzed. Alternatively, a material can be used for the separation member which can selectively separate biological sample components by their biological, chemical, or physical properties.

Figure 2:
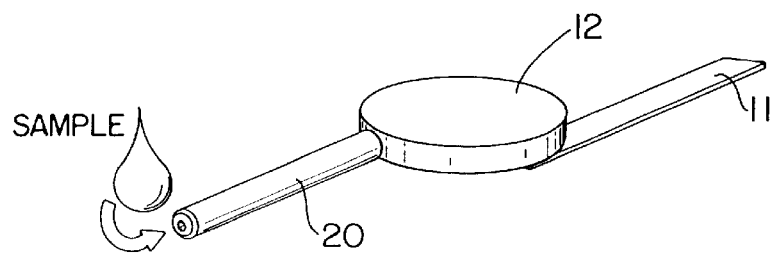
FIG. 2 shows a perspective view of an embodiment of the device according to the subject invention, termed the "single pad" configuration.

The single pad configuration of the subject invention, as shown in FIG. 2, comprises a separation member 12 and collection member 13 as described for the lateral flow configuration. However, this configuration further comprises a quantitation or wicking member 20 which can quantitatively load the sample onto the separation member. The wicking member is preferably a capillary tube which can advantageously provide a means for delivering a pre-determined volume of sample to the collection member. The inner wall of the capillary tube quantitation or wicking member can be coated with an anti-coagulant for facilitating migration of a whole blood sample through the separation member to the collection member.

Figure 3:
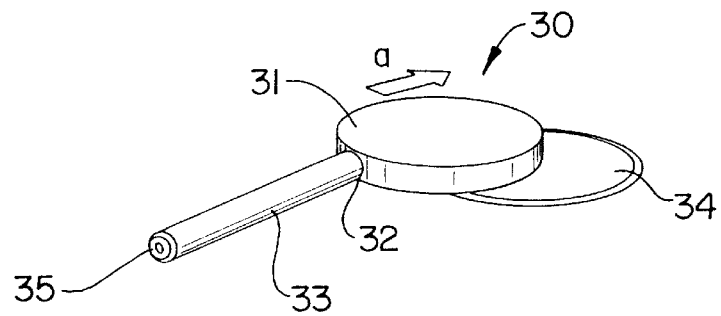
FIG. 3 shows a perspective view of a second embodiment (dual pad configuration) of a device according to the subject invention.

In a further embodiment of the subject invention, as shown in FIG. 3, the "dual pad" configuration of the subject device 30, comprises separation member 31, which is preferably abutting the second end 32 of capillary tube quantitation or wicking member 33, and is overlappingly in contact with the collection member 34. In this configuration, the sample is collected at the free end 35 of wicking member 33 and migrates by capillary action to separation member 31.

Preferably, the capillary tube volume is matched to the absorption capacity of the collection member. For example, we have identified that a capillary volume of about 30 μl is preferred to saturate, but not over-saturate, a collection member of certain materials. Specifically, a 20 μl capacity capillary tube will adequately saturate a 3/16 inch diameter collection member with sample, but does not sufficiently saturate a ¼ inch diameter collection member; optimal saturation of a collection member was obtained using a 30 μl capacity capillary tube for an approximately ¼ inch diameter collection member of Ahlstrom 319.

Preferably, the separation member 31 can separate sample constituents in a lateral direction (in a direction from the quantitation or wicking member, as shown by arrow a in FIG. 3) such that migration of undesired constituents, e.g., red blood cells, is retarded, allowing lateral passage of components of interest, e.g., analytes, to migrate onto collection member 34, which is at least partially overlapped by the separation member 31.

A variety of materials can be used for the separation member. These materials are preferably selected from glass fiber, glass fiber/cellulose mixtures, cellulose, or other proprietary materials, including synthetic materials, e.g., nylon.

Useful glass fiber materials include GF-24, GF-25, and #33, available from Schleicher & Schuell (Keene, N.H., USA); G143, G144, and G167, available from Ahlstrom (Mount Holly Springs, Pa., USA); GFQA30VA, GF/P 30, GF/DE 30, GF/SE 30, GF/CM30VA, GF/CM 30, F 075-14, GF DVA, GFVA 20, and GD-2, available from Whatman (Fairfield, N.J., USA); G 40, available from Micron Separation, Inc. (Westborough, Mass., USA); AP 25 and APFD, available from Millipore (Bedford, Mass., USA); and GC-90 and GA-200, available from Osmotics.

Useful glass fiber/cellulose mixture materials include F255-07 90 glass/10 cellulose, F255-09 70 glass/30 cellulose, F255-11 50 glass/50 cellulose, and F255-12 50 glass/50 cellulose, available from Whatman.

Useful cellulose materials include 598, available from Schleicher & Schuell. Miscellaneous or other materials falling outside the above categories can also be used, including HemaSep V and Leukosorb; which article of manufacture according to the subject invention available from Pall BioSupport (Port Washington, N.Y., USA).

One useful nylon material is Nylon 6.6 Transfer Membrane, which is commercially available under the tradename Biodyne B (Pall Gelman [location]). Another useful separation member is a track-etched membrane available from Whatman and commercialized as Cyclopore.

The separation member of the dual pad configuration can be selected from a variety of materials, including those described for the separation member used in the single pad configuration. In addition, the material known as "PlasmaSep", available from Whatman, can be used.

In one preferred embodiment, the separation member comprises an absorbent chromatography membrane or filter paper, e.g., HemaSep V (Pall BioSupport), which can separate constituents of a biological sample by size or binding characteristics which are well known in the art. The separation member is typically a substantially circular membrane, but is not limited by shape. HemaSep V is well-documented for its vertical separation characteristics (in the direction shown by arrow a in FIG. 1) and can be useful in the lateral flow configuration to separate serum or plasma from undesired sample constituents (cells) in the vertical direction such that serum or plasma flows downward from the top face of the separation member and onto the collection member contactingly disposed on the bottom face of the separation member. In the single and dual pad configurations, a preferred separation member selectively separates serum or plasma from undesired sample components (cells) in a lateral direction, i.e., in the direction of flow from quantitation or wicking member to collection member. HemaSep L (Pall BioSupport) can be used for this separation member, more preferably, a glass fiber filter material sold as GF-24 (Schleicher & Schuell). Preferably, constituents which are not desired to be analyzed (e.g., cells) are substantially bound or retained in the separation member, whereas an analyte in serum or plasma, is allowed to freely or selectively move with the separated plasma or serum through the membrane to the collection member.

The collection member used in the lateral flow configuration can be made from a variety of materials, including cellulose, polypropylene, nylon (including single or multi filament screens), polyester, modified polyester, polyethersulfone, nitrocellulose, high density polyethylene (HDPE), composites of natural and synthetic fibers.

Specifically, these materials can include DE81 and C/CM30, available from Whatman; 5 µm and 10 µm polypropylene, available from Millipore; Magna R 5 µm pore size Magna R 1.2 µm pore size, and 5 µm pore size, available from Micron Separation, Inc.; Loprodyne, HemaSep L, Accuwick 14-20, Accuwick 27-33, Accuwick 42-47, Predator, and Predator (plastic backed), available from Pall BioSystems; Biodyne B available from Pall Gelman; Cytosep 1660, Cytosep 1661, Cytosep 1662, and Cytosep 1663, Ahlstrom 319 available from Ahlstrom; X-4588, available from Porex; Nitex 3-8/1, Nitex 3-10/1, Nitex 3-15/5, Nitex 3-20/14, and 7-11F/826, available from Tetko.

In a preferred embodiment for a single pad or lateral flow configuration, the absorbent collection member is formed as an elongate or rectangular strip of material at least approximately 2 mm in width by at least about 10 mm in length. These dimensions are optimized to be capable of absorbing the total volume of separated sample. More preferably, the absorbent collection member is between about 3–5 mm in width and between about 25–45 mm in length. Most preferably, the absorbent collection member is about 4 mm in width by about 35 mm in length. The most preferred embodiment (4 mm×35 mm) of the collection member provides for an appropriate amount of liquid sample, e.g., a single drop of blood, to saturate but not over-saturate the collection member. Over-saturation occurs when the liquid front of the separated sample reaches the end of the strip, which can result in the analyte bunching up at the tip of the strip, making elution or analysis more difficult or inconsistent.

The collection member can also be pre-treated with a preservative or stabilizer to enhance stability or "shelf-life" of the separated sample or can be treated with a reagent to facilitate the release of the analytes from the member during the elution process. For example, devices intended for use in a protein assay can include a collection pad that is pre-treated with a reagent formulated to improve the stability of a protein in the sample. Other preservatives or stabilizers that can be used in the subject device include antioxidants, carbohydrates, buffers, other proteins, or the like, which are known in the art to provide a preservative or stabilizing effect on a biological sample. The release of the analytes from the collection pad can be enhanced with a pre-treatment of the collection member of a variety of surfactants.

In yet another alternative of the lateral flow configuration, the flow of sample applied to the device can be reversed, i.e., by applying sample to an elongate separation member. In this configuration, the elongate separation member can comprise an absorbent material capable of selectively retaining undesired sample component, e.g., red blood cells, and allowing fluid (serum or plasma) containing a component of interest to migrate to, and absorb into, a circular collection member.

For this configuration, it is preferred to use a known lateral flow membrane for the separation member. For example, GF-24 (Schleicher & Schuell) can be used and has been identified as a preferred separation member. As described, the separation member can be pre-treated with other reagents, e.g., surfactants to facilitate flow of sample through the member.

For the collection member, useful materials for the dual pad configuration include those described for use in the single pad configuration. In addition, certain highly absorbent materials were identified as providing advantageous results in the dual pad configuration. For example, Gelman Accuwick 14, Whatman BSM (also termed "PlasmaSep"), S&S 903, and Ahlstrom 319 can provide advantageous results.

Figure 4A:
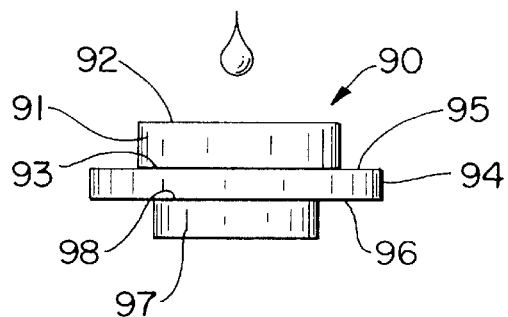
FIG. 4A shows a side view of a third embodiment (trilaminate variation of a multilaminate configuration) of a device according to the subject invention.

A still further embodiment of the subject invention concerns a multilaminate configuration which includes a separation member and quantitation member disposed directly over a collection member. One variation of this configuration is a trilaminate device shown in FIGS. 4A–4E. In FIG. 4A, a side view of the subject device in a trilaminate configuration 90 is shown. This configuration comprises a separation member 91 which is preferably a substantially flat, substantially circular disc made from material as described herein for a separation member. The separation member 91 has an outer face 92 for disposing a drop of biological sample, e.g., blood, thereon. The separation member 91 has a second face 93 which contacts the quantitation member 94 on its top face 95. A bottom face 96 of the quantitation member 94 is disposed so that it contacts the collection member 97. The collection member 97 can be an absorbent material as previously described.

Uniquely, this particular configuration can include a track-etched membrane or a screen material as the quantitation member 94. A track-etched membrane used in the trilaminate configuration of the subject device can be useful as an overflow member, i.e., to absorb excess volume of plasma transferred to the collection member. Typically, the track-etched membrane, e.g., Cyclopore (Whatman), is disposed between the separation member and the collection member, as it is preferred to employ the properties of the track-etched membrane following separation of cellular components from a blood sample. An additional advantage of the track-etched membrane is that it can serve as a filter to further separate any remaining cellular components which may not be removed from plasma or serum by the separation member or members.

Figure 4B:
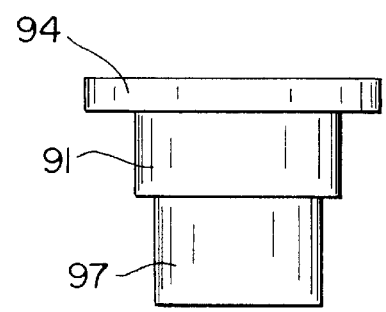
FIG. 4B shows a variation of the trilaminate configuration wherein the screen quantitation member is superimposed over the separation and collection members.

Use of a screen material for the quantitation member 94 can advantageously provide a means for applying consistent and accurate volumes of sample to the collection member 97. This consistent volumetric application can be achieved as a result of the structure of non-absorbent screen material used for the quantitation member 94. Examples of materials useful for a screen quantitation member include synthetic polymeric materials, e.g., nylon, polyester, or the like, which are commonly available having different pore sizes. For example, Tetko manufactures a plurality of nylon screens under the numerical designation 7-16/8; 7-5/2; 7-105/52; 7-280/44; and 7-200/44. Polyester screens available from Tetko include those designated 3-10/2; 3-5/1; and 3-20/14. A variation of this trilaminate configuration as shown in FIG. 4B, includes a device having a screen quantitation member 94 preferably disposed to overlay both the separation member 92 and collection member 97.

Use of a screen material can also have the advantage of serving as an indicator of minimum volume. A minimum volume of liquid sample can be indicated and applied to the device by calibrating relative distance or area of saturation on the overflow member. Accordingly, if a saturation spot does not reach a particular sized area on the overflow member, more sample may be necessary to provide a minimum volume of serum to the collection member for accurate measurement or determination of analyte.

Figure 4C:
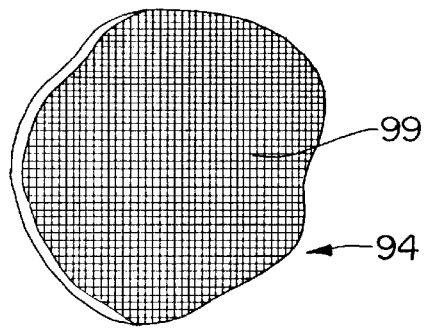
FIG. 4C shows an enlarged elevated view of a quantitation member formed from a screen material.

As shown in FIG. 4C, which is a magnified view of the pore structure forming the screen material of the quantitation member 94, liquid applied to the screen 94 spreads to cover the surface of the screen material and thereby distributes evenly into the pores 99 of the screen, formed by the cross-hatching structure of the screen material. Each of the pores can contain a fixed volume of liquid which is then absorbed onto the separation member 92 and collection member 97 disposed below the quantitation member 94.

Preferably, the separation member 92 has an upper face 98 which has a surface area smaller than the bottom face 96 of the quantitation member 94 and is smaller than the surface area of the spread liquid which is disposed onto the screen. Thus, when liquid sample is applied to the upper surface 95 of the quantitation member 94, the liquid spreads to cover an area larger than the surface area of the top face of the separation member 92. Therefore, only liquid sample contained in the pores of the screen material, which directly overlay the top surface of the separation member 92, is delivered to the collection member 97.

Figure 4D:
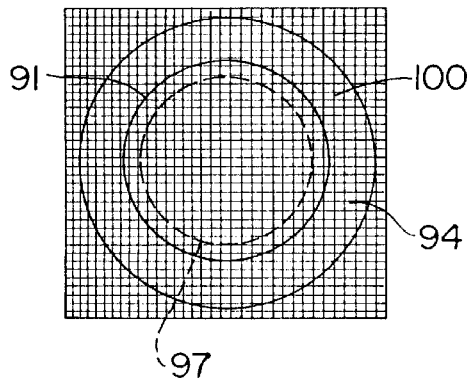
FIG. 4D shows a top plan view of a third embodiment (trilaminate variation of a multilaminate configuration) of a device according to the subject invention.
Figure 4E:
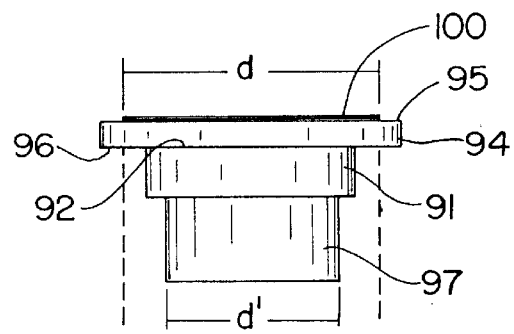
FIG. 4E shows a side view of a third embodiment (trilaminate variation of a multilaminate configuration) of a device according to the subject invention, illustrating the quantitative function achieved by the screen/collection member interface.

As shown in FIG. 4D, the liquid sample 100 spreading onto the quantitation member 94 has a surface area larger than the separation member 92 and the collection member 97 (shown in phantom). This is further illustrated in FIG. 4E, showing the liquid sample 100 covering an area having a diameter d which is larger than the width d' of the separation member 92 or collection member 97.

Figure 4F:
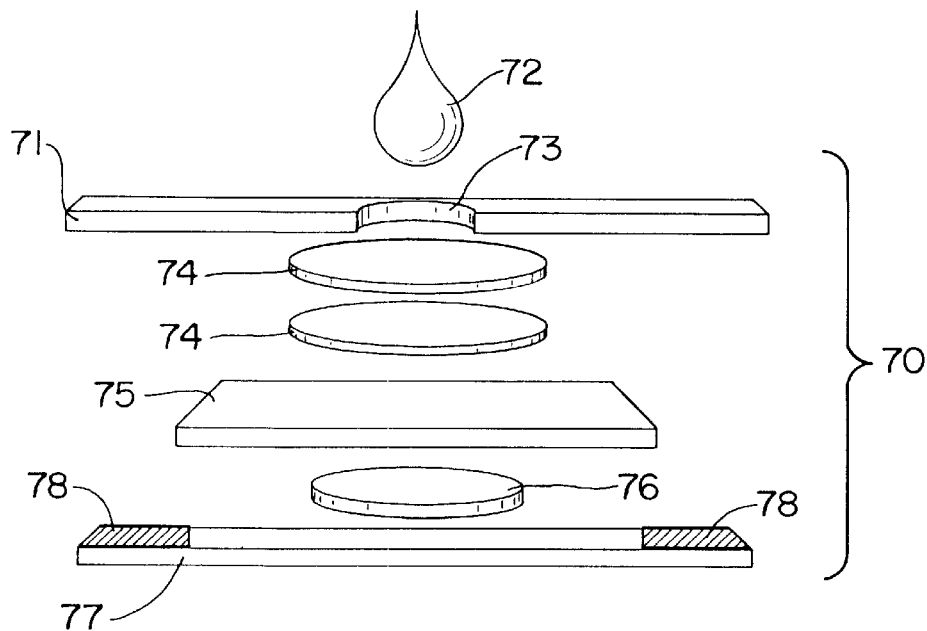
FIG. 4F shows an exploded perspective view of a multilaminate configuration of an embodiment of the subject invention comprising separation members, including an overflow member and a collection member adhered between cover members.
Figure 4G:
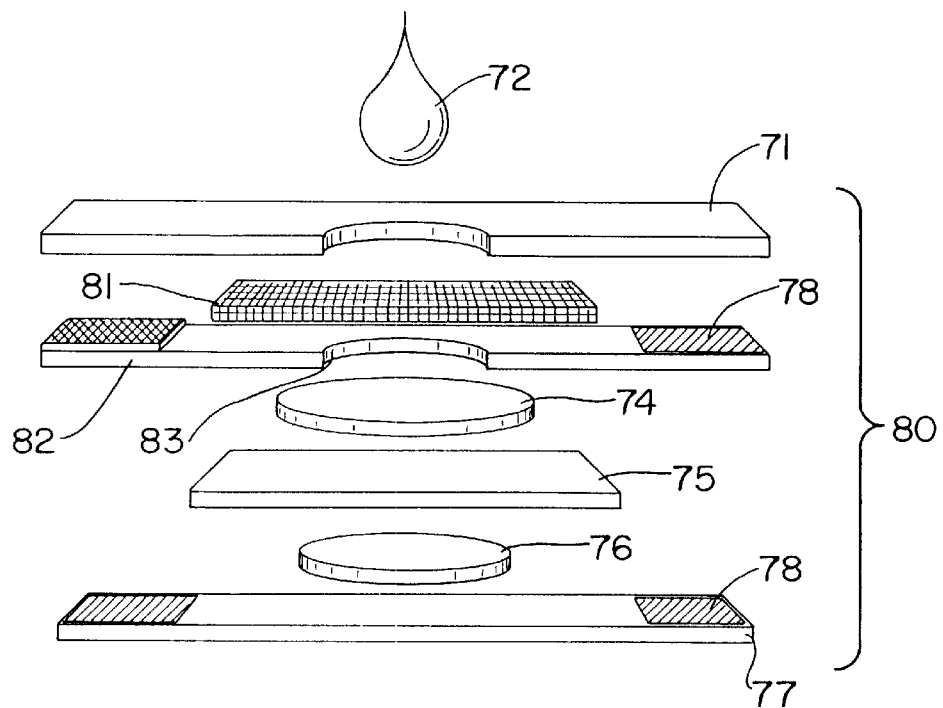
FIG. 4G shows an exploded perspective view of a multilaminate configuration of an embodiment of the subject invention comprising a screen member and an aperture liner member.

FIGS. 4F and 4G show variations of the multilaminate configuration having more than three members constituting the subject device. These are shown in exploded perspective view to illustrate each layer. In FIG. 4F, a multilaminate device 70 is shown comprising a top cover sheet 71 which can be made from a non-porous material, e.g., a polymer or plastic which is typically non-absorbent and non-permeable. The cover sheet 71 is shown as a sectional view. Sample 72, e.g., a drop of blood, is applied to the top face of the device so that it crosses the impermeable member 71 through an aperture or pore 73 formed thereon prior to construction of the laminated device.

The multilaminate configuration of the device as shown in FIG. 4F further comprises a separation member 74 which serves to separate and retain an undesired component, e.g., red blood cells, yet allow passage therethrough of a desired component, e.g., serum or plasma. FIG. 4F shows a device comprising two superimposed separation members 74. The separation members 74 can be the same or different materials, and are preferably independently selected from commercially available filter material described herein, e.g., GF 24, HemaSep V, Biodyne B, or the like.

In addition, the multilaminate device 70 comprises an overflow member 75 which can serve to absorb excess volume of liquid sample. The excess can be absorbed from liquid flowing from the separation member disposed in contact with the overflow member, or can absorb excess serum which oversaturates a collection member 76, contactingly disposed below the overflow member. The overflow member 75 can be made from filter material as described herein for a separation member. However, it is preferable to provide an overflow member which is equal to or greater in size than the separation member in order to function as an absorber of excess volume. The overflow member is preferably Cyclopore (Whatman).

The collection member 76 can also be made from material as described herein for a collection member used in other configurations of the subject device. Particular examples of materials that can be used as a collection member are Biodyne B or Ahlstrom 319.

The overflow member 75 can also be a screen material, having structure and properties as described herein. A non-permeable plastic or polymer can also be used to form the bottom layer or coversheet 77 of the subject device. Preferably, a coating of adhesive 78 can be applied to an inner face of coversheet 71 or 77 so that the cover sheets adhere together around the periphery of the other members. In one embodiment, adhesive can be omitted from one edge area so that the coversheets 71 and 78 do not permanently adhere at a particular location to facilitate removal of the collection member 75 from the unitary device.

In FIG. 4G a variation of the multilaminate configuration is illustrated, showing a device 80 according to the subject invention having a separation member 74, and overflow member 75, collection member 76, and top and bottom coversheets 71 and 77, respectively, as in FIG. 4F. However, this variation of the multilaminate configuration comprises a screen member 81 for evenly spreading the liquid sample, and an additional impermeable layer 82 which can serve as a liner for the screen member 81. Aperture 83 provided in line member 82 provides for fluid communication between screen member 81 and separation member 74. Further variations can include an additional screen member 81 or additional separation members 74.

Figure 4H:
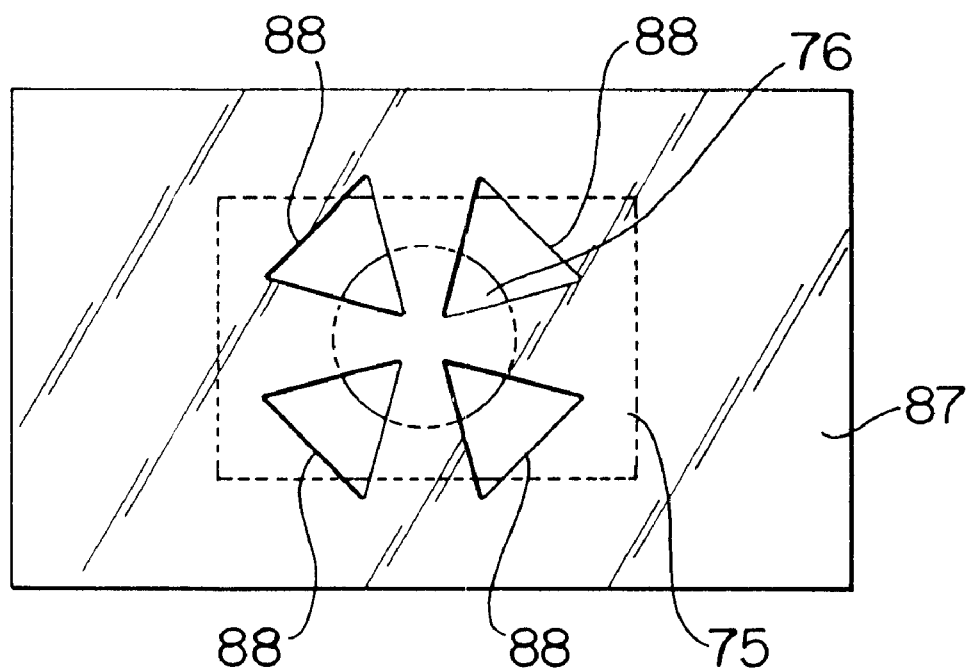
FIG. 4H shows an elevated view of a back face of a multilaminate configuration of the subject invention, illustrating a cut-out area for drying and removal of the collection member.

The embodiments of FIGS. 4F and 4G show a solid bottom coversheet 77. However, to facilitate drying of the collection member, which is advantageous in collecting substantially all of the separated screen or plasma from the sample, the bottom coversheet can be notched or apertured to provide communication between the collection member and the ambient air. The aperture or notch in the bottom coversheet can be various designs, but should provide the stated communication with ambient air while being capable of retaining the collection member in its position. A notch design which achieves this, and further allows access to the collection member for its removal from the device for conducting analysis on the collected serum is shown in FIG. 4H. In FIG. 4H, bottom coversheet 87 has a plurality of cut-out areas 88 which provide ambient air communication to the collection member 76 and overflow member 75, shown partially in phantom. It would be understood that other notch designs can also be useful to obtain said results of facilitating drying and accessing for removal of the collection member.

Figure 5A:
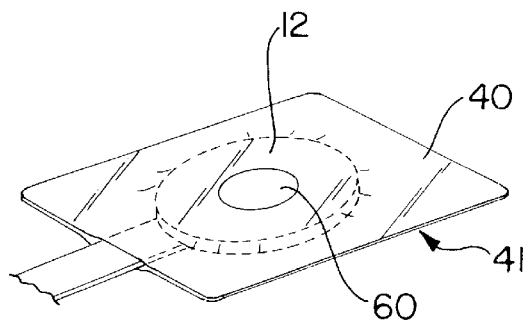
FIG. 5A shows a perspective view of a lateral flow configuration of the subject device having a cover laminated over top and bottom faces of the separation member.
Figure 5B:
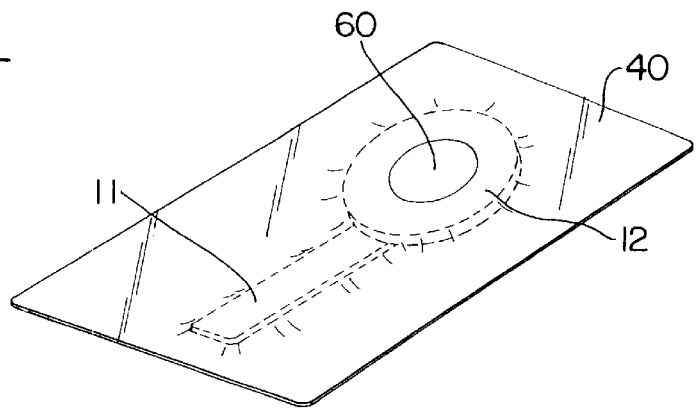
FIG. 5B shows a perspective view of a lateral flow configuration of the subject device having a cover laminated over top and bottom faces of the separation and collection members.
Figure 5C:
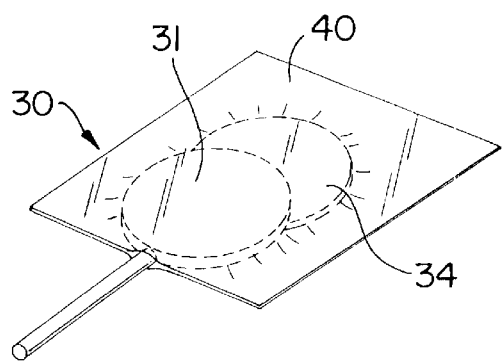
FIG. 5C shows a perspective view of a dual pad configuration of the subject device having a cover laminated over top and bottom faces of the separation member and collection member, having the wicking member extending therefrom.

A preferred device for any of the configurations described herein can include a cover sheet for protecting the absorbent collection or separation members. See, for example, FIGS. 5A–5C, which illustrate cover sheets included with the lateral flow and the dual pad configurations. In the lateral flow configuration, the covered subject device 41 includes a cover sheet 40 layered over the top and bottom faces of separation member 12 (FIG. 5A) or, more preferably, a cover sheet 40 layered over separation member 12 and collection member 11 (FIG. 5B). These are shown as having an aperture or perforation 60 in at least one cover sheet.

In a preferred embodiment for the dual pad configuration (FIG. 5C), the subject device includes cover sheet 40 layered over the top and bottom faces of separation member 31 and collection member 34. In one embodiment, cover sheet 40 comprises two separate sheets superimposed over and adhered to one another to completely encase the collection member or separation member (or both) of the subject device. It would be understood that the cover sheet can be formed by folding over a single sheet onto itself to form a double layer.

While a maximum size for the cover sheet can be determined as a matter of convenience of handling, at a minimum, the preferred cover sheet provides complete enclosure of these members in order to provide for proper migration of liquid sample and saturation of the collection member. Thus, for a lateral flow or single pad configuration, using a 6 mm diameter collection member, two 1 inch square sheets can be used. Alternatively, a rectangular sheet approximately 1 inch wide by approximately 1.5–2 inches long can be used to completely cover the separation member and elongate collection member.

For a dual pad configuration employing an approximately 6 mm diameter separation member and an approximately 6 mm diameter collection member, cover sheets approximately 1×1.5 inches is preferred. This allows for substantially complete closure of the sheets around the separation and collection members, while allowing the wicking member to extend from the cover sheet to facilitate collection of sample.

Any non-porous material, e.g., a polymeric or plastic material, can be used to form the cover sheets. To facilitate closure of the sheets around the perimeter of the collection or separation/collection members, an adhesive-backed plastic sheeting, which does not affect test results, can be used and cut to appropriate size for use. Such plastic sheeting material and adhesive material are well-known in the art. Moreover, the cover sheet advantageously functions to hold together the separate components of the subject device as a single unit. More preferably, an adhesive which can be released for removal of a collection member from therebetween can be used. For example, adhesive plastic 7843 (Adhesive Research, Glen Rock, Pa., USA) can be employed.

Figure 6A:
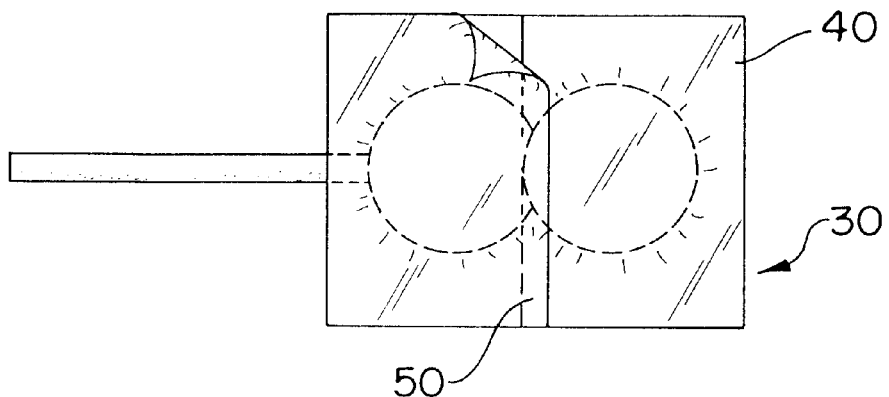
FIG. 6A shows an elevational view of a device according to the subject invention, illustrating a separable flap formed in one cover sheet for facilitating removal of a collection member.
Figure 6B:
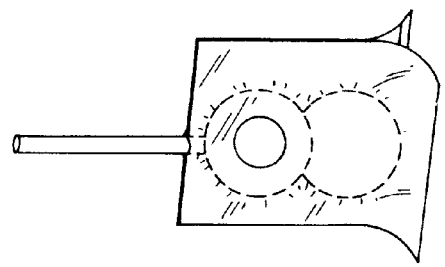
FIG. 6B shows an elevational view of a device according to the subject invention illustrating a separable flap formed by patternly disposed adhesive on the cover sheets which adheres the sheets together around the separation member, but allows separation of the sheets around the collection member.

In one alternative embodiment, which is illustrated in FIG. 6B, the sheets 40 are formed so as to provide a flap 50 on one side of the device 30 to facilitate release of the adhesive. In a preferred embodiment, as shown in FIG. 5B, adhesive is caused to be disposed on only a portion of the cover sheets such that a flap is formed at one end of said cover sheets, leaving one end unadhered and easily opened for removal of the collection member from between the cover sheets. The patternly disposed adhesive can be selectively applied at the end of the cover sheets which cover the separation member and the wicking member so that adherence is only made at the end covering these members. In the alternative, cover sheets having adhesive coated on their entire inner surface can be provided, and removal of adhesive from the collection member end can be carried out prior to adhering the cover sheets together.

Figure 7:
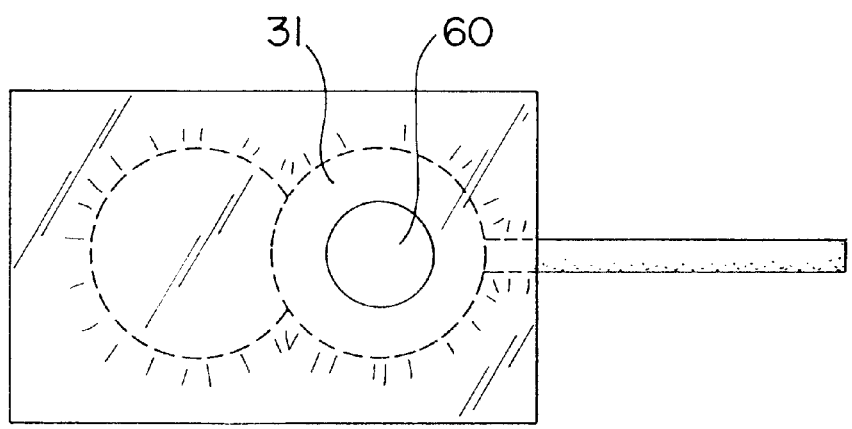
FIG. 7 shows an elevational view of an embodiment of the subject invention illustrating a perforation formed in the cover laminate.

Also on one side of the cover sheets, shown in FIG. 7, preferably a top side or a side opposite the flap 50, is a perforation or aperture 60 formed in the cover 40. This perforation 60, which is preferably formed in the portion of the plastic cover sheet to overlay the separation member, permits exposure to the air of the separation member in the dual pad configuration to facilitate or expedite drying of the sample which can be advantageous for preventing spill-over of undesired sample components (cells) onto the collection member, as well as application, transport, and analysis of the sample. In a preferred embodiment, the diameter of the perforation is approximately 60–75% of the diameter of the collection member. Alternatively, the perforation or aperture can be a plurality of holes formed within substantially the same diameter of the aperture shown in the Figures.

It would be readily understood by those of ordinary skill in the art that other dimensions could be used for any of the components forming the subject device, as long as those other dimensions are used routinely and consistently.

Figure 8A:
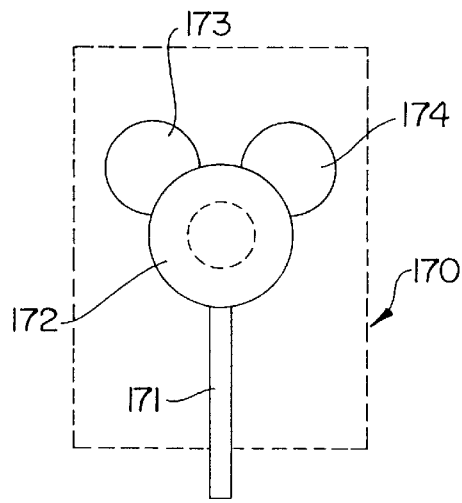
FIGS. 8A–8D show alternative configurations of a device according to the subject invention having a plurality of collection or separation members.
Figure 8B:
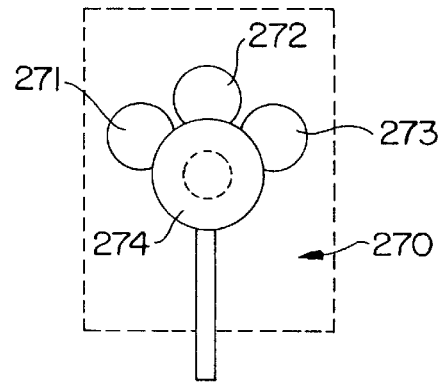

Variations of the subject device include embodiments having more than one collection member or more than one separation member. Certain of these variations contemplated for the subject invention are shown in FIGS. 8A–8D. For example, FIG. 8A shows a device 170 having a wicking member 171, separation member 172, and a pair of collection members 173 and 174 overlappingly disposed in contact with the separation member, but are positioned separate from each other at acute angles around the periphery of the separation member. FIG. 8B shows an alternative embodiment 270 to the configuration in FIG. 8A wherein three (3) collection members 271, 272, and 273 are overlappingly disposed in contact with the separation member 274.

Figure 8C:
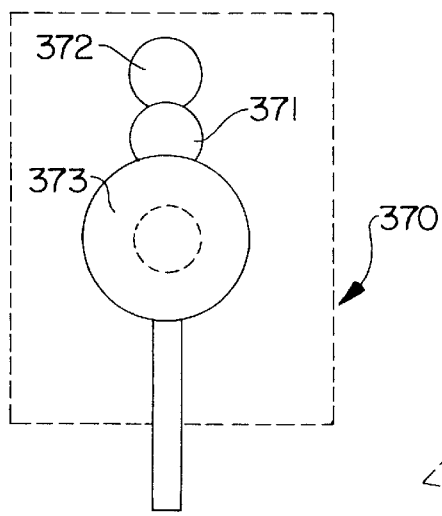

FIG. 8C shows an embodiment 370 wherein two collection members 371 and 372 are disposed sequentially relative to the separation member 373. The first collection member 371 is overlappingly in contact with separation member 373, and the second collection member 372 is in contact with the first collection member 371. Alternatively, this configuration could provide member 371 as a second separation member.

Figure 8D:
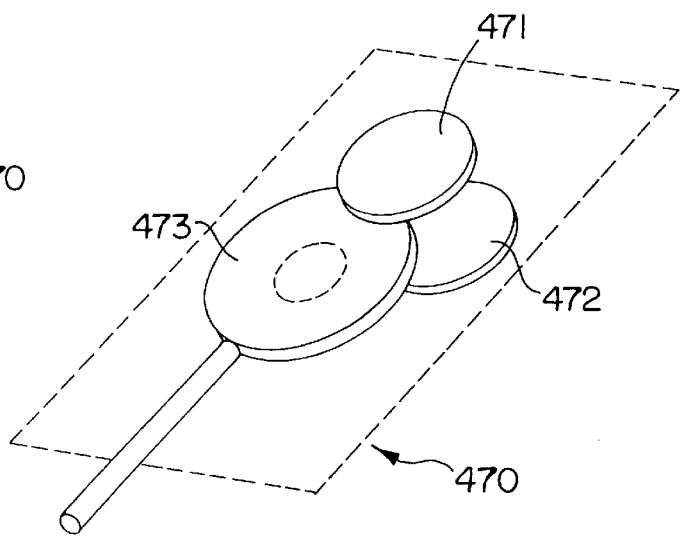
Figure 10:
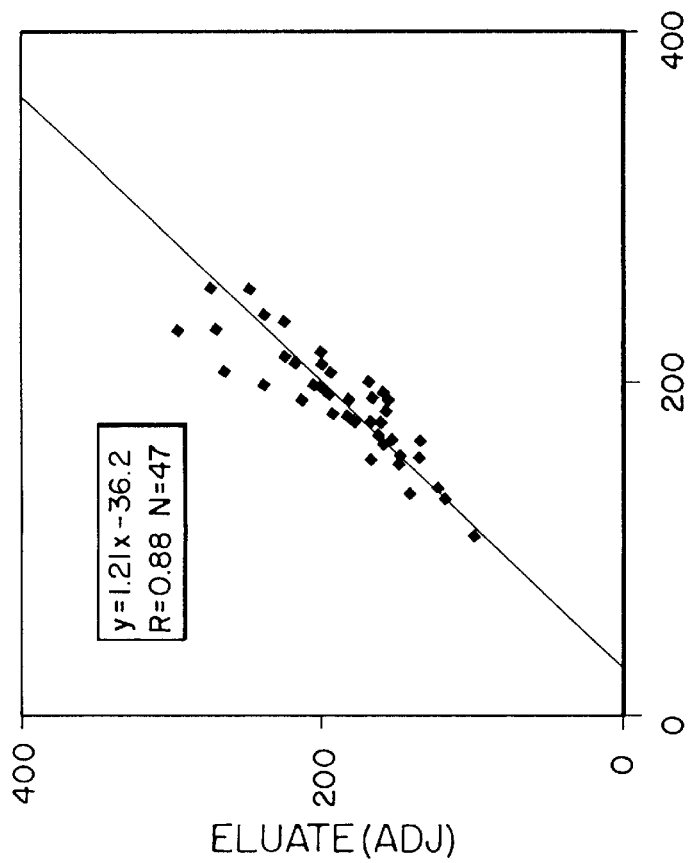
FIG. 10 shows regression analysis results for blood sample eluates (adjusted) vs. neat blood samples analyzed for cholesterol concentration using a single pad configuration of a device according to the subject invention.
Figure 9:
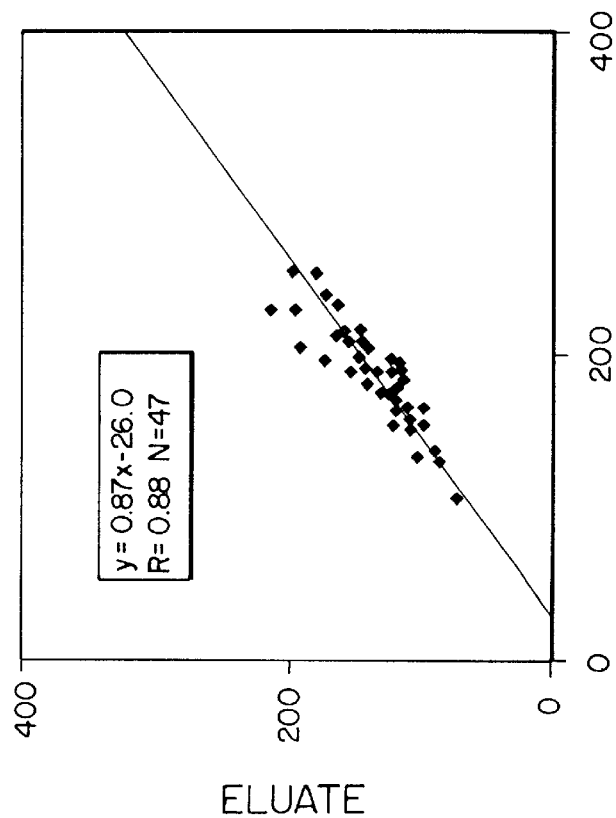
FIG. 9 shows regression analysis results for blood sample eluates vs. neat blood samples analyzed for cholesterol concentration using a single pad configuration of a device according to the subject invention.
Figure 12:
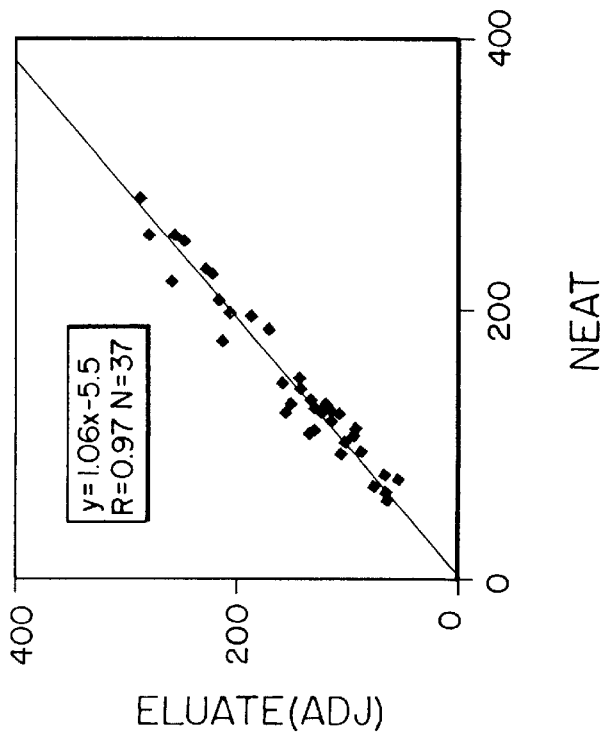
FIG. 12 shows regression analysis results for blood sample eluates (adjusted) vs. neat blood samples analyzed for triglyceride concentration using a single pad configuration of a device according to the subject invention.
Figure 11:
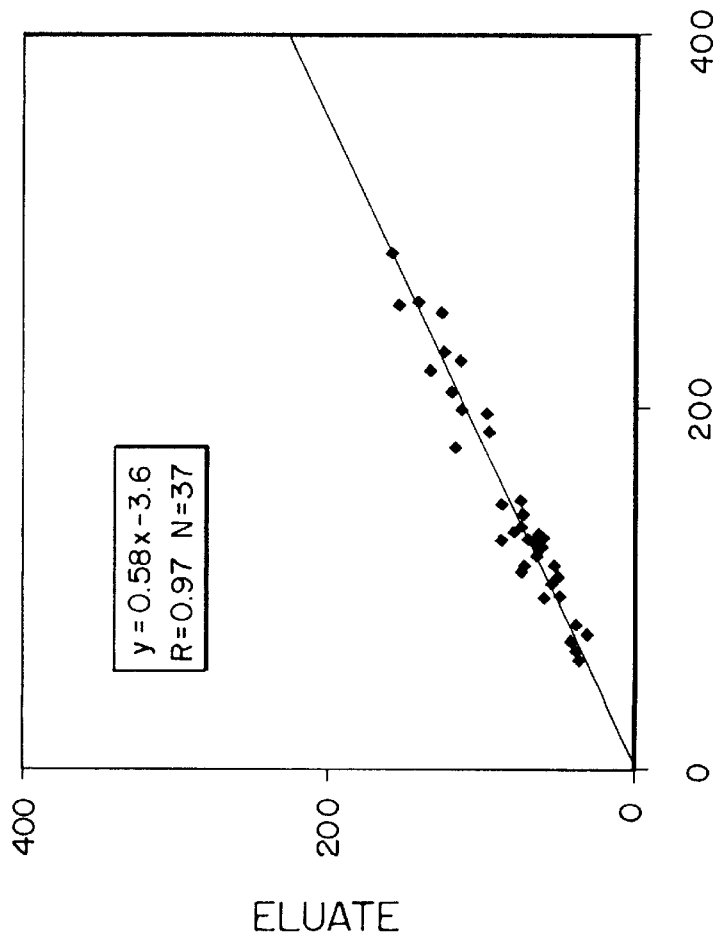
FIG. 11 shows regression analysis results for blood sample eluates vs. neat blood samples analyzed for triglyceride concentration using a single pad configuration of a device according to the subject invention.
Figure 14:
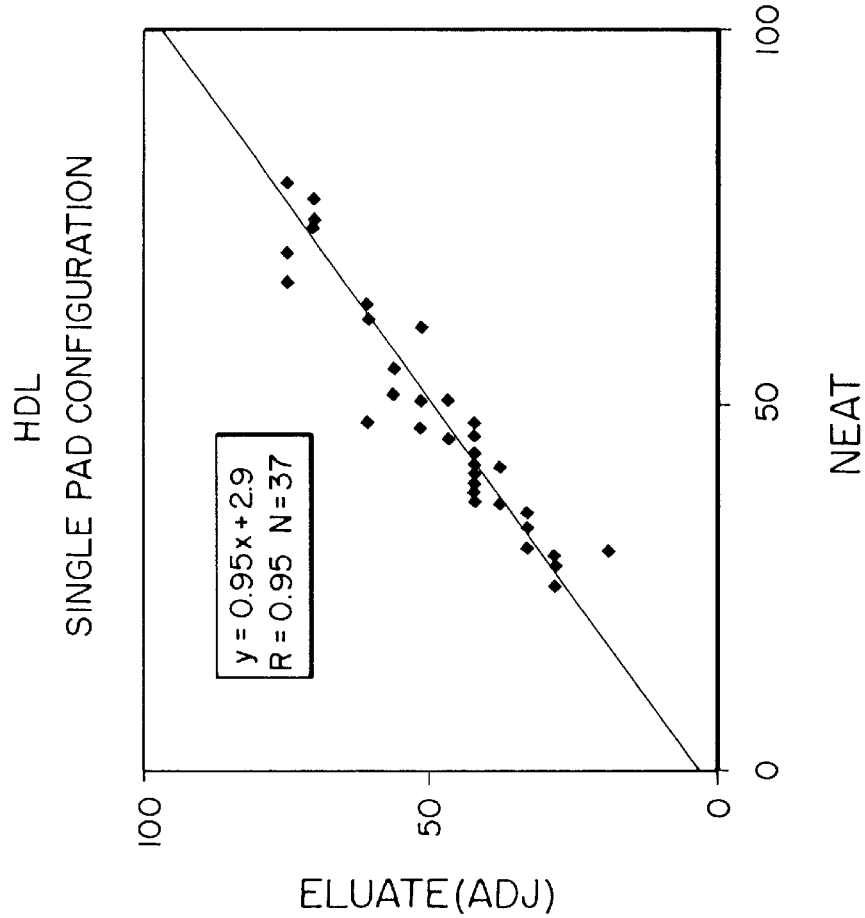
FIG. 14 shows regression analysis results for blood sample eluates (adjusted) vs. neat blood samples analyzed for HDL concentration using a single pad configuration of a device according to the subject invention.
Figure 13:
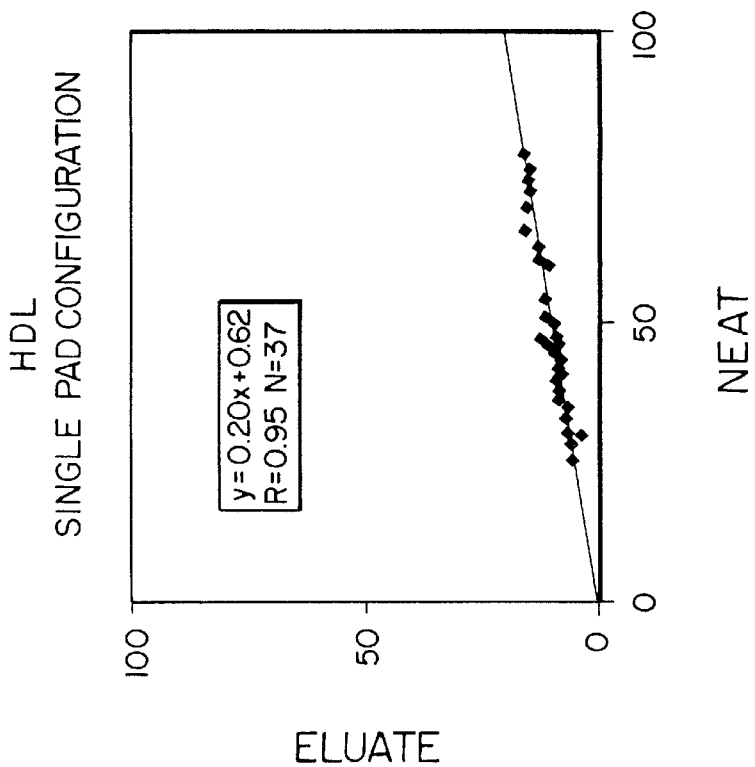
FIG. 13 shows regression analysis results for blood sample eluates vs. neat blood samples analyzed for HDL concentration using a single pad configuration of a device according to the subject invention.
Figure 16:
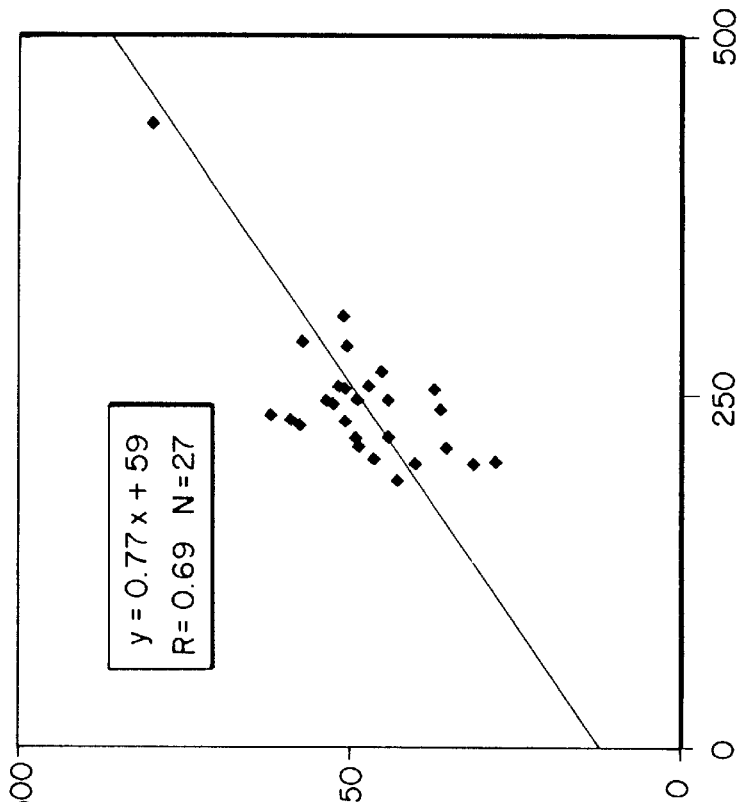
FIG. 16 shows regression analysis results for blood sample eluates (adjusted) vs. neat blood samples analyzed for fructosamine concentration using a single pad configuration of a device according to the subject invention.
Figure 15:
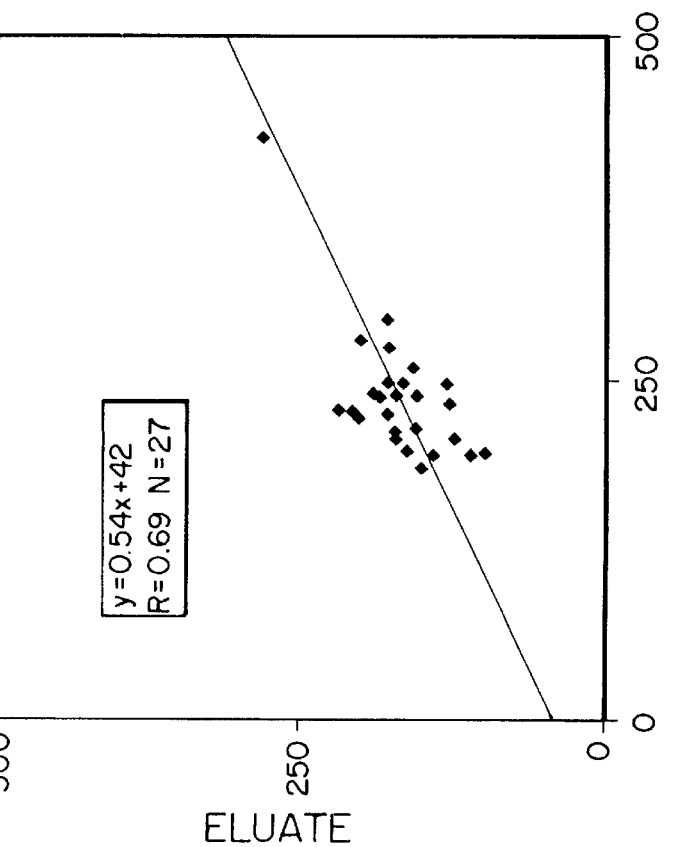
FIG. 15 shows regression analysis results for blood sample eluates vs. neat blood samples analyzed for fructosamine concentration using a single pad configuration of a device according to the subject invention.
Figure 18:
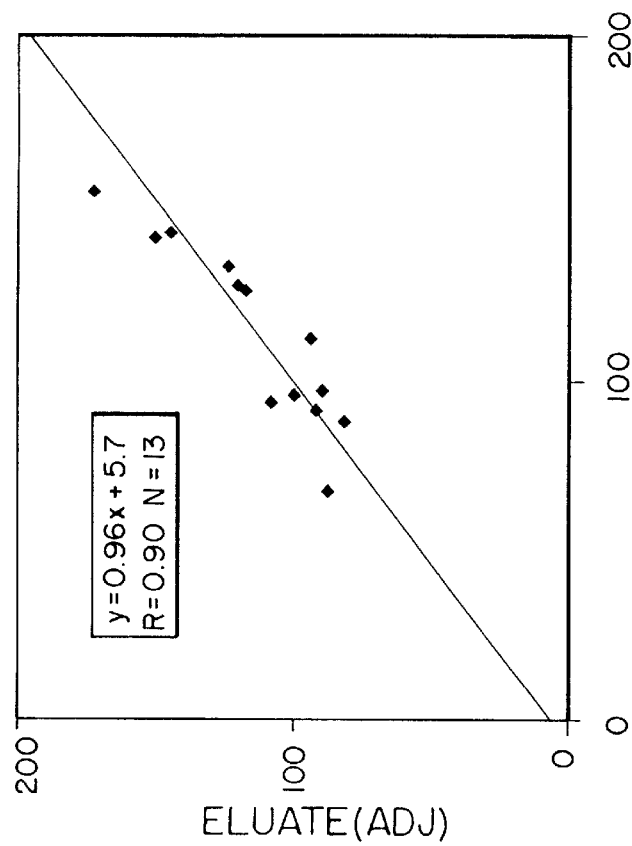
FIG. 18 shows regression analysis results for blood sample eluates (adjusted) vs. neat blood samples analyzed for direct LDL concentration using a single pad configuration of a device according to the subject invention.
Figure 17:
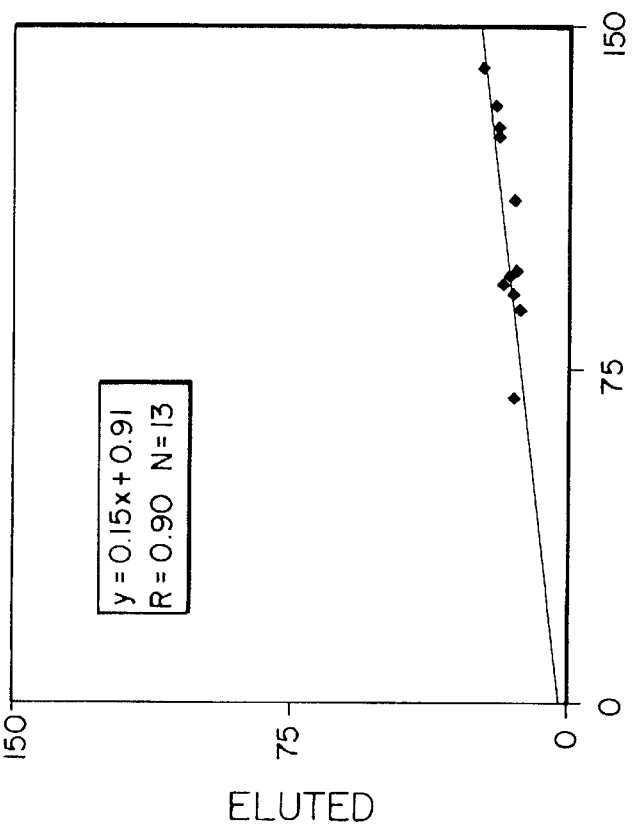
FIG. 17 shows regression analysis results for blood sample eluates vs. neat blood samples analyzed for direct LDL concentration using a single pad configuration of a device according to the subject invention.
Figure 20:
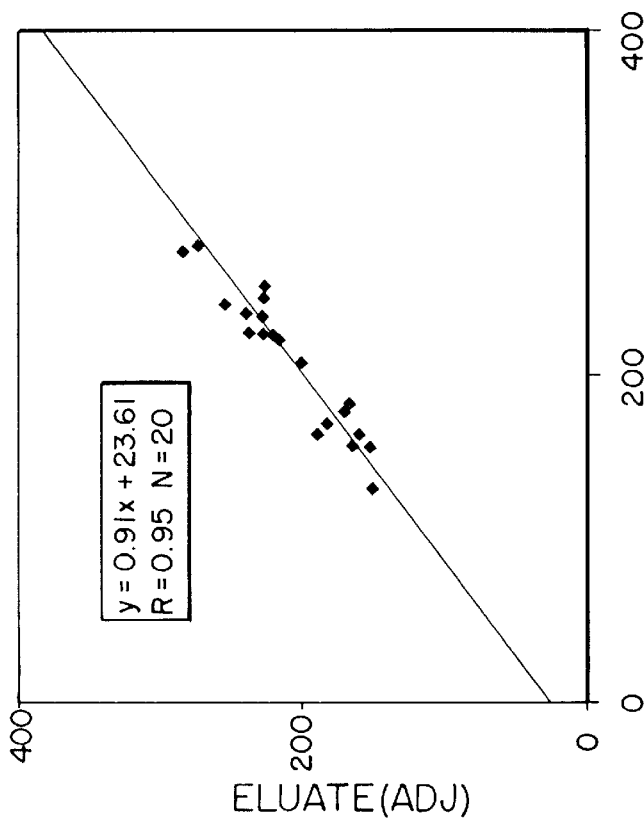
FIG. 20 shows regression analysis results for blood sample eluates (adjusted) vs. neat blood samples analyzed for cholesterol concentration using a dual pad configuration of a device according to the subject invention.
Figure 19:
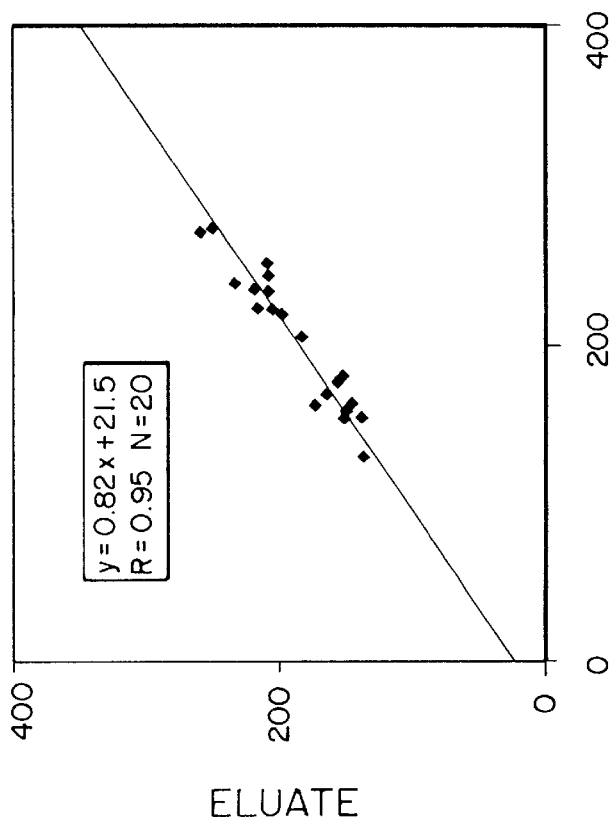
FIG. 19 shows regression analysis results for blood sample eluates vs. neat blood samples analyzed for cholesterol concentration using a dual pad configuration of a device according to the subject invention.
Figure 22:
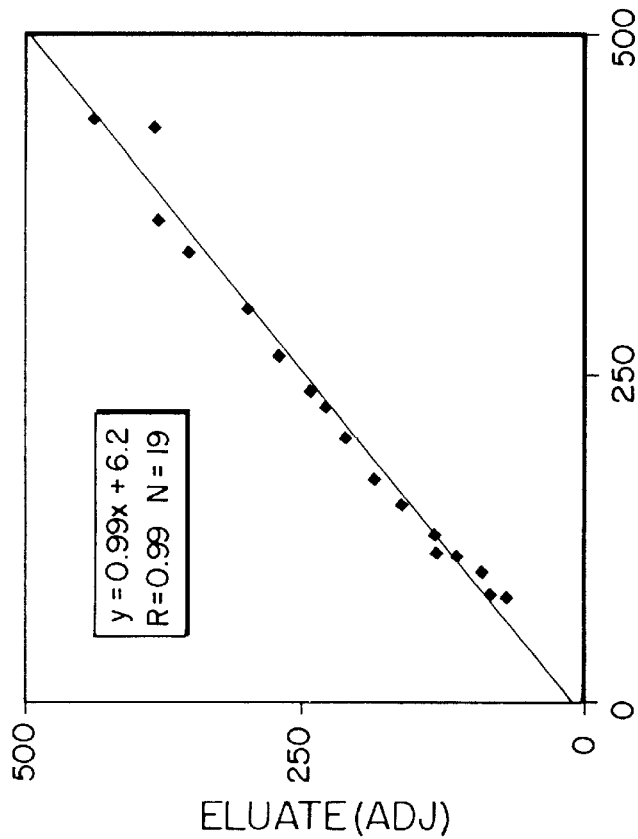
FIG. 22 shows regression analysis results for blood sample eluates (adjusted) vs. neat blood samples analyzed for triglyceride concentration using a dual pad configuration of a device according to the subject invention.
Figure 21:
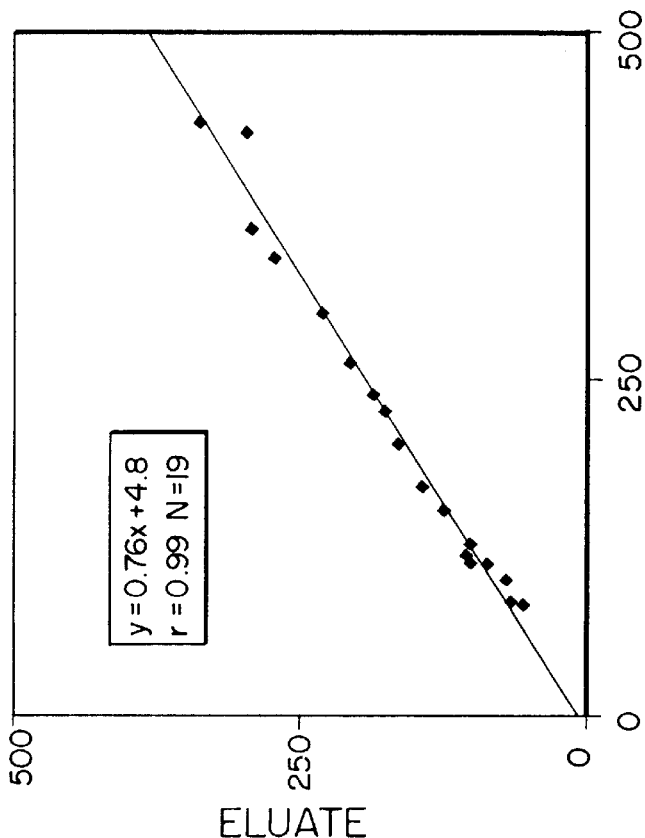
FIG. 21 shows regression analysis results for blood sample eluates vs. neat blood samples analyzed for triglyceride concentration using a dual pad configuration of a device according to the subject invention.
Figure 24:
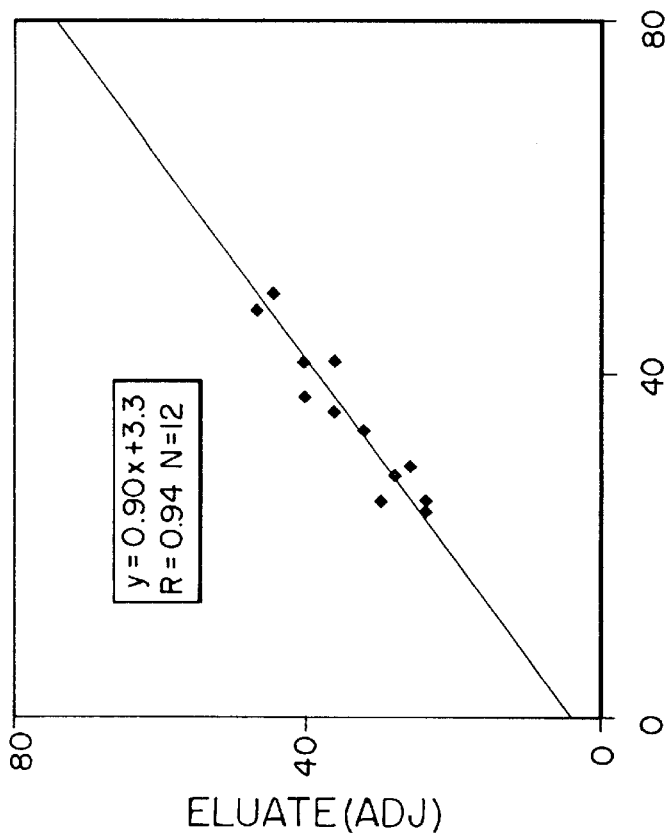
FIG. 24 shows regression analysis results for blood sample eluates (adjusted) vs. neat blood samples analyzed for ALT concentration using a dual pad configuration of a device according to the subject invention.
Figure 23:
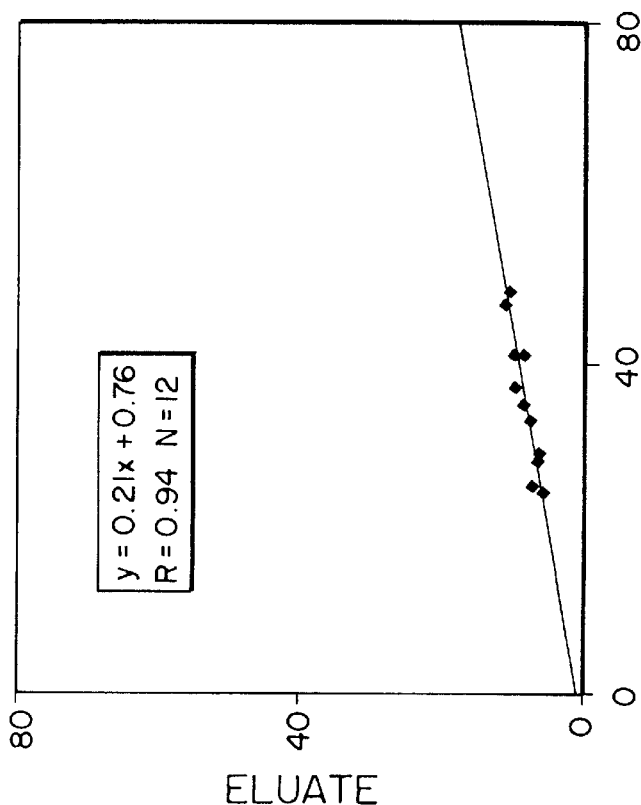
FIG. 23 shows regression analysis results for blood sample eluates vs. neat blood samples analyzed for ALT concentration using a dual pad configuration of a device according to the subject invention.

A further variation 470 shown in FIG. 8D shows a pair of collection members 471 and 472 overlappingly disposed in contact with opposing faces of the separation member 473.

To assemble the components of the lateral flow configuration of the subject device, the following steps are conducted:

(a) Peel the cover from the adhesive backing on the first plastic sheet, which includes the circular opening;

(b) Center the separation member, smooth side toward the adhesive side of the first plastic sheet, placing said member in a position to completely cover the circular opening, and pressing down firmly to secure said member in place.

(c) Place one end of the quantitation or wicking member in the center of the collection member such that the "tail" extends radially from the separation member. Cover the collection member and at least part of the quantitation or wicking member with a second sheet of the adhesive-backed plastic, superimposing the second and first sheets.

(d) Press down firmly to compress the quantitation or wicking and collection members at the point of contact. Secure adhesive around entire assembly with special attention given to the area immediately surrounding the collection member.

Thus, the lateral flow configuration is assembled "upside down", i.e. building the layers forming the device from the top face to the bottom face.

The single pad configuration can be assembled in an identical manner except that it includes, prior to application of the second cover sheet, providing a wicking member which is disposed to abut the separation member, diametrically opposite to the collection member.

For preparing a device having a dual pad configuration, similar steps are taken except that the device is assembled in a "right-side-up" manner, i.e., building the layers forming the device from the bottom face to the top face. Specifically, the collection member is first placed toward the center of an adhesive backed cover sheet forming the back face of the device, ensuring that the sheet will encase the collection member. A separation member is then overlapped onto the collection member and a quantitation or wicking member abutted thereagainst. A second, top cover sheet is then super-imposed over the first cover sheet and adhered thereto, ensuring that the entire separation member is covered by the cover sheets and that the aperture in the top cover sheet is positioned over the separation member. It is preferred that the top and bottom cover sheets are adhered together over the two faces of the device and are adhered together at least at the quantitation or wicking member end. Preferably, the adherence is from the end covering the quantitation or wicking member, extending about half the length of the cover sheet so as to provide a non-adhered section at the end of the cover sheets covering the collection member. An advantage to having adhesion on about half the area of the cover sheets is to facilitate removal of the collection member from the rest of the device for transporting the collection member to a laboratory for analysis.

The multilaminate configuration can be assembled by using a cover sheet as a base and layering the component members over one another in a desired configuration. The multilaminate configuration can be assembled from top to bottom or from bottom to top. Apertures or other cut-out areas or shapes of the component members are preferably pre-formed prior to assembly. Preferred layering sequences are illustrated in FIGS. 4A–4H.

The subject method for using a device according to the subject invention as described herein comprises applying, either directly or indirectly, a liquid sample to the separation member, allowing the liquid sample to separate thereon and substantially saturate the collection member, allowing the separation member and collection members to dry, for at least two hours, preferably overnight, at room temperature after collection of the sample, and then shipping, typically by mail, the dried separation and collection members to a facility for analysis.

Use of configurations of the subject device comprising a capillary tube as a quantitation or wicking member include contacting a liquid sample to the free end of the quantitation or wicking member and allowing the sample to migrate to and substantially saturate the separation member. The remaining steps are substantially identical for all other configurations of the subject device.

Clinical analysis using the device of the subject invention is achieved through a series of steps that allow for the specific quantification of sample components as captured by the collection member.

Specifically, when the device and sample are received at the analytical facility, the dried collection member is removed from the device assembly, components of interest are extracted from the collection member. Extraction of the analyte is typically achieved by eluting the analyte of interest into a liquid eluent, e.g., water, aqueous buffer, reactive reagent, inorganic or organic solvent, or the like. Analysis of the extract is usually performed by established clinical methodologies, with values adjusted according to the dilutions made. Analyses of blood components (analytes) from a sample of whole blood using the subject device can include, but are not limited to, determining presence or absence (and if present, quantification of) total cholesterol, triglyceride, bone alkaline phosphatase, high density lipoprotein (HDL) cholesterol, low density lipoprotein (LDL) cholesterol, ALT, glucose and fructosamine. Analyses can be performed with the use of a commercially available blood chemistry analyzer, e.g., Roche Cobas Mira Plus Chemistry Analyzer, using readily recognized modifications of established assay parameters. Results of analyses of samples assayed for certain typically assayed blood components are shown in FIGS. 9–24, demonstrating comparable results using a device of the subject invention versus standard liquid blood sample analysis.

Following are examples which illustrate procedures for practicing the invention. These examples should not be construed as limiting. All percentages are by weight and all solvent mixture proportions are by volume unless otherwise noted.

EXAMPLE

Empirical Results Using Subject Device

Various materials for use as a component of the subject device were shown to successfully absorb separated sample, e.g., serum or plasma, from the wicking or separation member. Optimal plasma migration is obtained when the collection member is positioned to overlap the separation member by approximately 1 mm. Plasma migration was only about 50% as successful when the separation member and collection member abutted to one another rather than over-lapped.

The device performed superiorly when encased in a minimum of about 1.5" of plastic cover sheet material. Substantially complete enclosure of the device is required for the migration of the serum using a GF24 separation member contacting the collection member.

A low degree of "spill over" was observed using the device of the subject invention. Spill-over is defined here as the migration of red blood cells onto the collection pad immediately following blood application.

Hemolysis was observed after more than 24 hours of drying time when the cover sheets were not perforated. Hemolysis is defined as an overall redness that appears on the collection member over time, distinguishing it from "spill-over" which is evident at the point of contact at the time of blood application. All devices were free of hemolysis on the day of spotting. Overall, the degree of hemolysis is much less with the dual pad configuration than was observed with the single pad configuration.

Hemolysis was shown to be virtually eliminated with the incorporation of the perforation punched into the plastic cover sheet placed directly over the separation or collection member.

In addition, imprecision between replicates is greatly improved with the new dual pad configuration as compared to the single pad configuration. Sensitivity of cholesterol and triglyceride is adequate employing the 30 $\mu$l capillary tube as a wicking member and a ¼ inch collection member. It is compromised somewhat with the use of the smaller devices, i.e., 20 $\mu$l blood: 3/16" collection pads. A decrease in elution volume would compensate for this loss in sensitivity if a low volume application is necessary.

Sonification vs. shaking studies were performed to determine whether the imprecision between replicate spots could be attributed to incomplete elution of cholesterol from the collection member. Initial data show improvement when sonification is employed.

It should be understood that the examples and embodiments described herein are for illustrative purposes only and that various modifications or changes in light thereof will be suggested to a person of ordinary skill in the art and are to be included within the spirit and purview of this description.

What is claimed is:

1. A device for quantitative remote-site collection and drying of a liquid biological sample obtained from an individual for the purpose of mailing for recovery and laboratory analysis of an analyte contained in the biological sample, said device comprising:
    a separation member which selectively separates and retains an undesired component in the sample from a component of interest containing analyte; and
    a non-reactive collection member for collecting and drying the separated analyte-containing component of interest, wherein said dried collection member can be later at least partially removed from the device to recover the analyte-containing component for laboratory analysis of analyte.

2. The device of claim 1 wherein the biological sample is whole blood and the component of interest is plasma or serum.

3. The device of claim 1 wherein the separation member is capable of separating and substantially permanently retaining cellular components in the biological sample without leaching of said cellular components into the collection member.

4. The device of claim 1 wherein the separation member is an absorbent filter material.

5. The device of claim 1 wherein the separation material is selected from glass fiber, glass fiber/cellulose mixtures, cellulose, or synthetic materials.

6. The device of claim 4 wherein the separation member is glass fiber.

7. The device of claim 1 wherein the collection member is made from a material selected from cellulose, polypropylene, nylon, polyester, modified polyester, polyethersulfone, nitrocellulose, high density polyethylene, or a composite of natural and synthetic fibers.

8. The device of claim 1 wherein at least one of said members is pre-treated with a reagent which facilitates the collection, separation, storage, transport, preservation, recovery, or analysis of the sample.

9. The device of claim 1 further comprising a substantially impermeable cover.

10. The device of claim 9 wherein said cover further comprises an aperture which is superimposed over the top face of a separation member when the cover is placed in position on the device.

11. The device of claim 1 further comprising a quantitation member in contact or fluid communication with the separation member for quantitatively delivering the sample to the separation member.

12. The device of claim 11 wherein the quantitation member is a capillary tube.

13. The device of claim 11, wherein the quantitation member is a non-absorbent screen material.

14. The device of claim 11, wherein the quantitation member is a track-etched membrane.

15. The device of claim 1 wherein the analyte is selected from bone alkaline phosphatase, cholesterol, triglyceride, high density lipoprotein, low density lipoprotein, fructosamine, and alanine amino transferase.

16. The device of claim 1 wherein said device comprises a plurality of collection members in contact or fluid communication with a single separation member.

17. The device of claim 1 wherein said device comprises a plurality of separation members.

18. The device of claim 1, said device further comprising an overflow member to absorb excess volume of liquid sample.

19. A method for quantitative remote-site collection of a biological sample and laboratory analysis of an analyte in the sample, said method comprising:
    providing a collection device to an individual or a health care professional, said device comprising a separation member which selectively separates and retains an undesired component in the sample from the component of interest containing the analyte, and a separable collection member for collecting the analyte-containing component of interest which has been separated from the undesired component, wherein said separation member and collection member are in contact or fluid communication with one another for delivering the analyte-containing component of interest from the separation member to the collection member;

applying the biological sample in liquid form to the device so that the analyte-containing component of interest is quantitatively collected onto the collection member;

drying said collection member having the analyte-containing component of interest collected thereon;

transporting the collection member to a facility for analysis of the analyte;

removing the collection member from the device;

eluting the analyte from the collection member;

determining presence, absence, or concentration of the analyte; and reporting results of the analysis to the individual or health care professional.

20. The method of claim 19 wherein the drying step can be completed before the step of removing the collection member.

21. The method of claim 19 further comprising identifying the individual and sample by a code.

22. The method of claim 19 wherein the elution step is modified according to the particular component of interest being determined.

23. The method of claim 19 wherein the step of determining presence, absence, or concentration of the analyte is modified according to said particular component.

24. A kit for quantitative remote-site collecting of a biological sample from a patient for laboratory analysis of said sample, said kit comprising:

a device for quantitative remote-site collection and drying of a liquid biological sample obtained from an individual for the purpose of mailing for recovery and laboratory analysis of an analyte contained in the biological sample;

a separation member which selectively separates and retains an undesired component in the sample from a component of interest containing analyte;

a non-reactive collection member for collecting and drying the separated analyte-containing component of interest, wherein said dried collection member can be later at least partially removed from the device to recover the analyte-containing component for laboratory analysis of analyte; and an information card for providing information about the patient.

25. The kit of claim 24 wherein said kit further comprises a component selected from a lancet, antiseptic swab, and packaging means for transporting the collected sample.

* * * * *

UNITED STATES PATENT AND TRADEMARK OFFICE
CERTIFICATE OF CORRECTION

PATENT NO. : 6,036,659  
DATED : March 14, 2000  
INVENTOR(S) : Robert A. Ray, Robert Stangarone, Julie Peddicord, and Raul Sarzo Page 1 of 1

It is certified that error appears in the above-identified patent and that said Letters Patent is hereby corrected as shown below:

Column 14,
Line 32: replace 6B with --6A--.
Line 34: replace 5B with --6B--.

Signed and Sealed this

Thirty-first Day of July, 2001

*Attest:*

NICHOLAS P. GODICI
*Attesting Officer*     *Acting Director of the United States Patent and Trademark Office*